(12) United States Patent
Kasbergen et al.

(10) Patent No.: US 12,179,034 B2
(45) Date of Patent: Dec. 31, 2024

(54) DEVICE FOR VISION TRAINING AND THERAPY

(71) Applicant: Light Tree Ventures Holding B.V., The Hague (NL)

(72) Inventors: Michael Kasbergen, Schoonhoven (NL); Alain Dijkstra, Amstelveen (NL)

( * ) Notice: Subject to any disclaimer, the term of this patent is extended or adjusted under 35 U.S.C. 154(b) by 407 days.

(21) Appl. No.: 17/830,950

(22) Filed: Jun. 2, 2022

(65) Prior Publication Data

US 2022/0387814 A1  Dec. 8, 2022

Related U.S. Application Data

(60) Provisional application No. 63/196,693, filed on Jun. 4, 2021.

(51) Int. Cl.
*A61N 5/06* (2006.01)

(52) U.S. Cl.
CPC ........ *A61N 5/06* (2013.01); *A61N 2005/0626* (2013.01); *A61N 2005/0632* (2013.01); *A61N 2005/0648* (2013.01); *A61N 2005/0652* (2013.01); *A61N 2005/0658* (2013.01)

(58) Field of Classification Search
CPC .............. A61N 5/06; A61N 2005/0626; A61N 2005/0632; A61N 2005/0648; A61N 2005/0652; A61N 2005/0658; A61N 2005/0633; A61N 2005/0662

See application file for complete search history.

(56) References Cited

U.S. PATENT DOCUMENTS

| 5,986,581 | A | * | 11/1999 | Magdaleno, II | B64F 1/18 362/249.14 |
|---|---|---|---|---|---|
| 8,317,320 | B2 | | 11/2012 | Huang | |
| 10,279,192 | B2 | | 5/2019 | Malchano et al. | |
| 2004/0012758 | A1 | * | 1/2004 | Lin | G02C 7/14 351/203 |
| 2014/0071398 | A1 | * | 3/2014 | Glassco | G02C 3/006 351/157 |
| 2018/0193664 | A1 | * | 7/2018 | DiMauro | A61N 5/0622 |
| 2020/0094015 | A1 | * | 3/2020 | Colbaugh | G16H 20/40 |
| 2020/0108272 | A1 | * | 4/2020 | Bahmani | A61N 5/0622 |
| 2020/0238101 | A1 | * | 7/2020 | Schoutens | G02C 11/10 |

* cited by examiner

*Primary Examiner* — Paula J Stice
*Assistant Examiner* — Ranjani Mari Sundaresan
(74) *Attorney, Agent, or Firm* — Pasadena Legal Group; Norman R. Van Treeck

(57) ABSTRACT

A device, for vision training and therapy, comprises a spectacle frame including a left rim, a right rim, and a bridge connecting the left rim and the right rim, wherein the left rim and the right rim include a plurality of therapeutic light sources located along the left rim and the right rim, for providing light therapy to the eyes of a user, a longitudinal member connected with the spectacle frame, and extending away from the spectacle frame, along the line of sight of the user, wherein the longitudinal member includes a plurality of colored light sources connected by a white stripe arranged to be viewable by both eyes of the user and a controller connected with the plurality of therapeutic light sources and the plurality of colored light sources. Further, the longitudinal member is extendible through an extension mechanism attached to the spectacle frame.

14 Claims, 14 Drawing Sheets

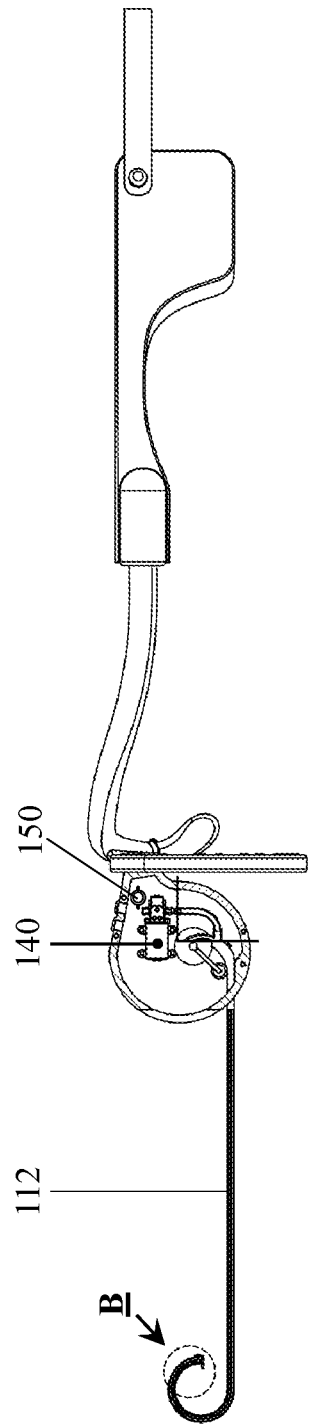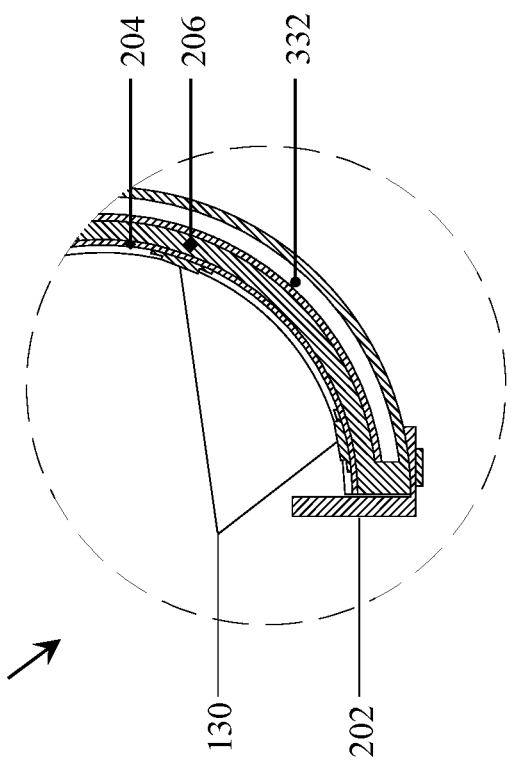
Fig. 3B
Fig. 3C

DEVICE FOR VISION TRAINING AND THERAPY

TECHNICAL FIELD

The present invention generally relates to vision training and therapy devices. More specifically, the present invention relates to devices that are designed to train the vision of the user for several different scenarios, while also providing light-based therapy to the eyes of the user.

BACKGROUND ART

Vision problems are often equated with conditions that diminish eyesight, like nearsightedness, farsightedness, astigmatism, presbyopia, and a variety of eye diseases. However, like most issues affecting health, the majority of vision problems are caused by or significantly contributed to by stress. The human eye is genetically designed for three-dimensional vision and has been historically used mainly for seeing at distance. Thus, any activity that primarily confines vision to only two dimensions at a near distance, like focusing on books, cell phones, or computers for extended periods, results in visual fatigue and stress, leading to eyesight deterioration.

The human eye was not designed to read or work at a computer all day. Yet, educational and occupational demands stress our eyes by forcing them to focus at a close distance for prolonged periods. But visual stress does not just fatigue our eyes on a subjective level. It also fatigues the cells of our eyes, reducing their ability to produce the energy required to fuel our eye's ability to aim, track, focus, and team, so we can see efficiently. As a result of the widespread use of computers and handheld devices, deteriorating vision is now the world's largest health epidemic and is continually growing. Ian Morgan of Australian National University reported in the journal Lancet that up to 90 percent of young adults in China, Taiwan, Japan, Singapore, and South Korea are nearsighted.

Currently, two-thirds of the US population wears glasses, yet less than 1 percent are born needing them. Virtually all Americans under age sixty use computers and as many as 90 percent complain about eyestrain. These statistics are comparable to computer users in Europe. According to the International Telecommunication Union, there are almost as many cell-phone subscriptions (6.8 billion) as there are people on this earth (7 billion). Just as physical training reduces stress, while improving speed, strength, and flexibility, vision training has the same effect. Since vision is the body's guidance system, improving visual performance affects everything we do. Whether we're keeping our eye on the ball in sports, judging distance while driving, or tracking a line of print while reading or computing, visual efficiency is the key to our success. By fine-tuning our vision, we optimize our performance and maximize our potential. But vision training is only one way to reduce visual stress. You can also counteract the effects of stress on the eyes, by optimizing cellular function through the process of photobiomodulation. Photobiomodulation in the eye primarily involves the interaction of red and near-infrared light with the cell's mitochondria. Since vision deterioration is linked to mitochondrial dysfunction, and the eyes contain the body's greatest concentration of mitochondria, current research confirms that red and near-infrared light have a powerful impact on our eyes.

Conventional techniques for addressing vision stress and eyesight deterioration include wearing glasses or contact lenses or undergoing surgery. In any case, notwithstanding the risks and potential for incorrect diagnoses involved, such techniques only provide temporary relief, until there is a time again for a newer pair of glasses or an additional surgery. Vision training and photobiomodulation, on the contrary, reduce visual stress, improve vision performance, and have the potential to reverse the degrading effect of aging on the eyes and vision with no side effects. Vision training has also gained popularity in the field of professional sports where attributes such as peripheral awareness, dynamic visual acuity, depth perception, hand-eye coordination, and contrast sensitivity are required.

However, even though there are several vision training exercises in the art, they are rarely adaptable to the individual needs of a person and are often vague. Moreover, most of the vision training exercises require supervision by an experienced trainer. This makes vision training only available to small sections of society who can incur the additional rather heavy expenditure. Few devices in the market would enable any layman to avail the therapeutic benefits of vision training, without spending large sums of money.

Therefore, there is a need in the art for a novel device for vision training and therapy that does not suffer from the aforementioned deficiencies.

OBJECTS OF THE INVENTION

Some of the objects of the present invention are listed below:

It is an object of the present invention to provide a multi-purpose device that serves to both train human vision for better cognizance of their surroundings, but also treat the eyes for therapeutic purposes;

It is another object of the present invention to provide a device that is beneficial for both personal and commercial use;

It is yet another object of the present invention to provide a device that is simple in construction, configuration and operation; and It is a furthermore object of the present invention to provide a device that is convenient to use.

Other objects, features, advantages, and goals of the present invention will be better understood from the following detailed description taken in conjunction with the accompanying drawings.

SUMMARY

According to an aspect of the present invention, there is provided a device for vision training and therapy, the device comprising a spectacle frame including a left rim, a right rim, and a bridge connecting the left rim and the right rim. The left rim and the right rim include a plurality of therapeutic light sources located along the left rim and the right rim, for providing light therapy to the eyes of a user. The device further includes a longitudinal member connected with the spectacle frame, located below the bridge of the spectacle frame, and extending away from the spectacle frame, along the line of sight of the user. The longitudinal member includes a plurality of colored light sources connected by a white strip arranged to be viewable by both eyes of the user. The device also includes a controller connected with the plurality of therapeutic light sources and the plurality of colored light sources. The controller is configured to sequentially control the display of each of the plurality of colored light sources, arranged in a linear arrangement, to both eyes of the user. Also, the longitudinal member is extendible through an extension mechanism attached to the spectacle frame.

In one embodiment of the invention, the plurality of therapeutic light sources is configured to emit electromagnetic radiation with wavelengths in the range of 630 nm to 880 nm.

In one embodiment of the invention, the longitudinal member and the extension mechanism are included in a housing detachably attached with the spectacle frame.

In one embodiment of the invention, the attachment and the detachment of the housing is adapted to be achieved through one or more snap-fit arrangements, loop and hook fasteners based arrangements, spring-loaded clips based arrangements, sliding arrangements, and magnetic coupling based arrangements.

In one embodiment of the invention, the extension mechanism further includes a spool including a coil spring adapted to roll out and roll in the longitudinal member, a locking button connected with a locking arrester via a flexible member. The flexible member is adapted to keep the locking arrester biased against the longitudinal member. Also, in use, when the locking button is pressed downward, a convex shape of the flexible member is adapted to cause the locking arrester to move upwards and release the longitudinal member.

In another embodiment of the invention, the extension mechanism further includes a spool adapted to roll out and roll in the longitudinal member, a pneumatic pump configured to generate pressurized air, an air inlet pipe connecting the pneumatic pump with an inlet nozzle provided at an inlet to an air cavity of the longitudinal member, and a lever is adapted to lock the longitudinal member once the longitudinal member has been extended to a predetermined length. Also, in use, the supply of pressurized air from the pneumatic pump into the air cavity is adapted to cause an extension of the longitudinal member.

In one embodiment of the invention, the plurality of therapeutic light sources is configured to emit electromagnetic radiation in the infrared range of wavelengths of the electromagnetic spectrum.

In one embodiment of the invention, the plurality of therapeutic light sources are separated from each other by a distance varying between 0.002 inches and 1.00 inches, along the left rim and the right rim. In some embodiments, the left rim and the right rim may also include continuous light sources such as neon tubes, flexible light strip where the distance between the light sources is negligible and emits therapeutic radiation.

In one embodiment of the invention, the plurality of colored light sources is separated from each other by a distance varying between 2 inches and 8 inches, along with the longitudinal member.

In one embodiment of the invention, the plurality of therapeutic light sources and the plurality of colored light sources include a plurality of Light Emitting Diodes (LEDs). In other embodiments, therapeutic radiation can also be provided by optical fibers.

In one embodiment of the invention, the controller is further configured to control the emission characteristics of the plurality of therapeutic light sources and the plurality of colored light sources in response to user input.

In one embodiment of the invention, the user input is received through a control interface provided with the device.

In one embodiment of the invention, the user input is received from a remote communication device connected with the device through a communication network.

In one embodiment of the invention, the device has a wearable configuration, where the device is worn on the user's head using a headband. The headband can be made of a stretchable material allowing the device to properly fix on the user's head and fits accordingly.

In an alternate embodiment of the invention, the device can also be incorporated as a handheld device, where the device is gripped by the user. In this embodiment, the device includes a handle provided at the bottom surface of the housing which is being held or gripped by the user during vision training and therapy session.

In the context of the specification, the term "Light Emitting Diodes (LEDs)" refers to, and include, through-hole type LEDs (generally used to produce electromagnetic radiations of red, green, yellow, blue, and white colors), Surface Mount LEDs, Bi-color LEDs, Pulse Width Modulated RGB (Red-Green-Blue) LEDs, and high power LEDs, etc. The LEDs may also be provided on an Organic LED (OLED) based flexible panel or an inorganic LED-based flexible panel. Such OLED panels may be generated by depositing organic semiconducting materials over Thin Film Transistor (TFT) based substrates. Further, discussion on the generation of OLED panels can be found in Bardsley, J. N (2004), "*International OLED Technology Roadmap*", *IEEE Journal of Selected Topics in Quantum Electronics*, Vol. 10, No. 1, that is included herein in its entirety, by reference. An exemplary description of flexible inorganic light-emitting diode strips can be found in granted U.S. Pat. No. 7,476,557 B2, titled "Roll-to-roll fabricated light sheet and encapsulated semiconductor circuit devices", which is included herein in its entirety, by reference. The LEDs may also be micro-LEDs described through U.S. Pat. Nos. 8,809,126 B2, 8,846,457 B2, 8,852,467 B2, 8,415,879 B2, 8,877,101 B2, 9,018,833 B2, and their respective family members, assigned to NthDegree Technologies Worldwide Inc., which are included herein by reference, in their entirety. The LEDs in that regard may be provided as a printable composition of the micro-LEDs, printed on a substrate.

In the context of the specification, terms like "light", "radiation", "irradiation", "emission" and "illumination", etc. have been used synonymously and refer to electromagnetic radiation in a frequency range varying from the Ultraviolet (UV) frequencies to Infrared (IR) frequencies and wavelengths, wherein the frequency range is inclusive of UV and IR frequencies and wavelengths. It is to be further noted here that UV radiation can be categorized in several manners depending on respective wavelength ranges, all of which are envisaged to be under the scope of this invention. For example, UV radiation can be categorized as, Hydrogen Lyman-α (122-121 nm), Far UV (200-122 nm), Middle UV (300-200 nm), Near UV (400-300 nm). The UV radiation may also be categorized as UVA (400-315 nm), UVB (315-280 nm), and UVC (280-100 nm). Similarly, IR radiation may also be categorized into several categories according to respective wavelength ranges which are again envisaged to be within the scope of this invention. A commonly used subdivision scheme for IR radiation includes Near IR (0.75-1.4 µm), Short-Wavelength IR (1.4-3 µm), Mid-Wavelength IR (3-8 µm), Long-Wavelength IR (8-15 µm), and Far IR (15-1000 µm).

In the context of the specification, the term "silicone" represents polymers made up of siloxane (—R2Si—O—SiR2-, where R=organic group).

In the context of the specification, the term "processor" is considered to be inclusive of a general-purpose processor, a Field Programmable Gate Array (FPGA), an ARM-based processor, or an Application Specific Integrated Circuit (ASIC), etc.

In the context of the specification, the term "memory unit" is considered to be inclusive of volatile memory units such as Static Random Access Memory (SRAM) and Dynamic Random Access Memory (DRAM) of types such as Asynchronous DRAM, Synchronous DRAM, Double Data Rate SDRAM, Rambus DRAM, and Cache DRAM, etc.

In the context of the specification, the term "communication interface" is considered to include ports such as Universal Serial Bus (USB) port, Video Graphics Array (VGA) port, and High Definition Multimedia Interface (HDMI) port for wired connections. The communication interface may also include modems for wireless communication, such as a Wireless Fidelity (Wi-Fi) modem for data transfer or a GSM modem for mobile telephony, and GPRS modems for connecting to the Internet or other Wide Area Networks through protocols standardized by 3GPP.

In the context of the specification, the term "communication network" is considered to be inclusive of Local Area Networks (LANs) be implemented through several short-range wired or wireless communication protocols such as Ethernet, ZigBee, Bluetooth, Wireless Fidelity (Wi-Fi), and Near Field Communication (NFC), etc. and Wide Area Networks (WANs) implemented through protocols standardized by the $3^{rd}$ Generation Partnership Project, such as HSPA, HSDPA, LTE, and the like or through protocols standardized by IEEE such as 802.11 Wi-Fi and 802.3 Ethernet or the like.

In the context of the specification, the term "sound transducer" is considered to be a device that is used to convert an electrical signal into a sound wave and a sound wave into an electrical signal.

In the context of the specification, the term "program" is considered to be a series of coded software instructions to control the operation of an electronic device or other machines.

The following detailed description is illustrative and is not intended to be in any way limiting. In addition to the illustrative aspects, embodiments, and features described above, further aspects, embodiments, and features will be apparent by reference to the following detailed description in conjunction with the accompanying drawings.

BRIEF DESCRIPTION OF THE ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which:

FIG. 3B illustrates a central sectional view of the wearable device of FIG. 3A;

FIG. 3C illustrates a detailed view of a portion of the wearable device of FIG. 3B;

Figure 1A:
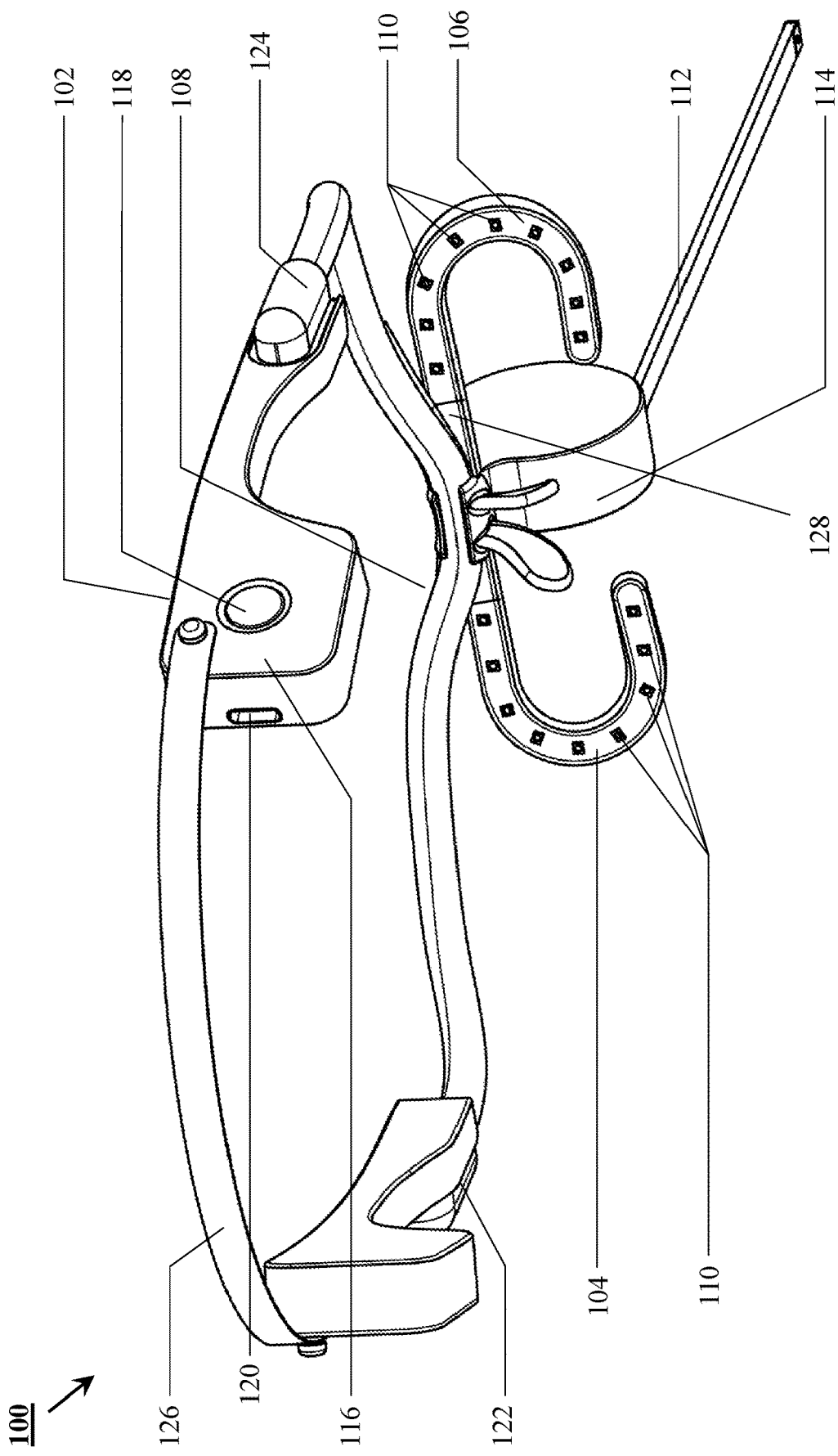
FIG. 1A illustrates a rear perspective view of a wearable device for vision training and therapy, in accordance with an embodiment of the present invention.

While the present invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention.

DETAILED DESCRIPTION

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure.

It is envisaged that a wearable device be provided that includes a combination of an extendible longitudinal member having several colored light sources to train the eyes of a user, and a spectacle frame with several therapeutic light sources on a left and a right rim to provide therapeutic benefits to the eyes. For example, the longitudinal member may have ten (10) 660 nm Light Emitting Diodes (LEDs) positioned every 3.0 inches apart. The left and the right rims of the spectacles may include a series of 630 nm~880 nm LED's positioned 0.04 inches apart from each other. In several embodiments, the left and the right rim may include an alternate series of 660 nm LED's and 830 nm LED's. This alternate arrangement of the LEDs allows the user to see a circle in space created by the 660 nm LEDs, while receiving the therapeutic effect of the 830 nm LEDs. The wearable device would serve several purposes. For example, they will passively train high-level attention by creating a virtual sight in space, affording the user visual feedback about their eye teaming skills. And while the user's visual skills are being optimized, the cells of their eyes will be nourished by wavelengths of light that increase the production of energy fueling their function. Once the LED's on the left and the right rims and the longitudinal member turn on, the eyes of the user will visually track the colored LED's on the longitudinal member as they slowly move away and then towards the user. The training portion of this system will provide different exercises e.g. sequential, alternating, far-near, and random.

Further, it is envisaged that a handheld device is provided including a spectacle frame having a left rim and a right rim, wherein each rim includes a plurality of therapeutic light sources positioned at the periphery of the rims. The therapeutic light sources are positioned 0.04 inches apart from each other and emit radiation in the wavelength range of 630 nm~880 nm. The handheld device further includes a longitudinal member that extends from a housing that is connected to the spectacle frame through a connecting member. The longitudinal member includes a plurality of colored light sources positioned at equidistance to each other and emits light in a sequential manner to provide a plurality of exercises for vision training. The handheld device further includes a handle physically connected to the bottom surface of the housing, which is being gripped by a user during vision training and therapy session. Referring to the figures, both the embodiments of the invention will now be described in further detail.

FIG. 1A illustrates a rear perspective view of a wearable device 100 for vision training and therapy, in accordance with an embodiment of the present invention. As illustrated in FIG. 1A, the wearable device 100 includes a spectacle frame 102, a left rim 104, and a right rim 106. A bar 108 of the spectacle frame 102 is detachably attached with a bridge 128. The bridge 128 is the point where the left rim 104 and the right rim 106 connects. In alternate embodiments, the left rim 104 and the right rim 106 can also act as a single unit. The spectacle frame 102 also includes a left temple 122 and a right temple 124, which receives the respective ends of the bar 108. The spectacle frame 102 further includes a headband 126 that allows a user to worn the spectacle frame 102 on their heads. The headband 126 is made up of a stretchable material and is curved in shape. However, a person skilled in the art would appreciate that the presence of the headband 126 is to enable the wearable device 100 to be used by users with heads of different sizes, in a customized construction of the wearable device 100, the headband 126 may not be essential. There is also provided a controller 116 within the wearable device 100. The controller 116 has been provided at one side of the spectacle frame 102, though the location of the controller 116 may vary from one design to another, being within the scope of the present invention. The controller 116 has been provided with a control interface 118 and a charging port 120. The control interface 118 may be a tactile button capable of physical motion (such as being pressed like electrical switches or rotated like jog dials and radio tuners) or maybe a touch-based interface. The spectacle frame further includes an inbuilt rechargeable battery which is charged via the charging port. The charging port 120 may have a Universal Serial Bus (USB) A, B, or C type design or any other proprietary design depending upon the application of the wearable device 100.

The left rim 104 and the right rim 106 include a plurality of therapeutic light sources 110 located along the inner surfaces of the left 104 and the right 106 rims that are supposed to be facing towards the user. In several embodiments of the present invention, the plurality of therapeutic light sources 110 may include Light Emitting Diodes (LEDs). The plurality of therapeutic light sources 110 may be configured to emit electromagnetic radiation between Ultraviolet (UV) and Infrared (IR) wavelengths of the electromagnetic spectrum. In several embodiments, the plurality of therapeutic light sources 110 are separated from each other by a distance varying between 0.002 inches and 0.08 inches, along the left rim 104 and the right rim 106. The wearable device 100 further includes a longitudinal member 112 extending from a housing 114 connected with the spectacle frame 102. The longitudinal member 112 is located below the bridge 128 of the spectacle frame 102, and extends away from the spectacle frame 102, along the line of sight of the user.

Figure 1B:
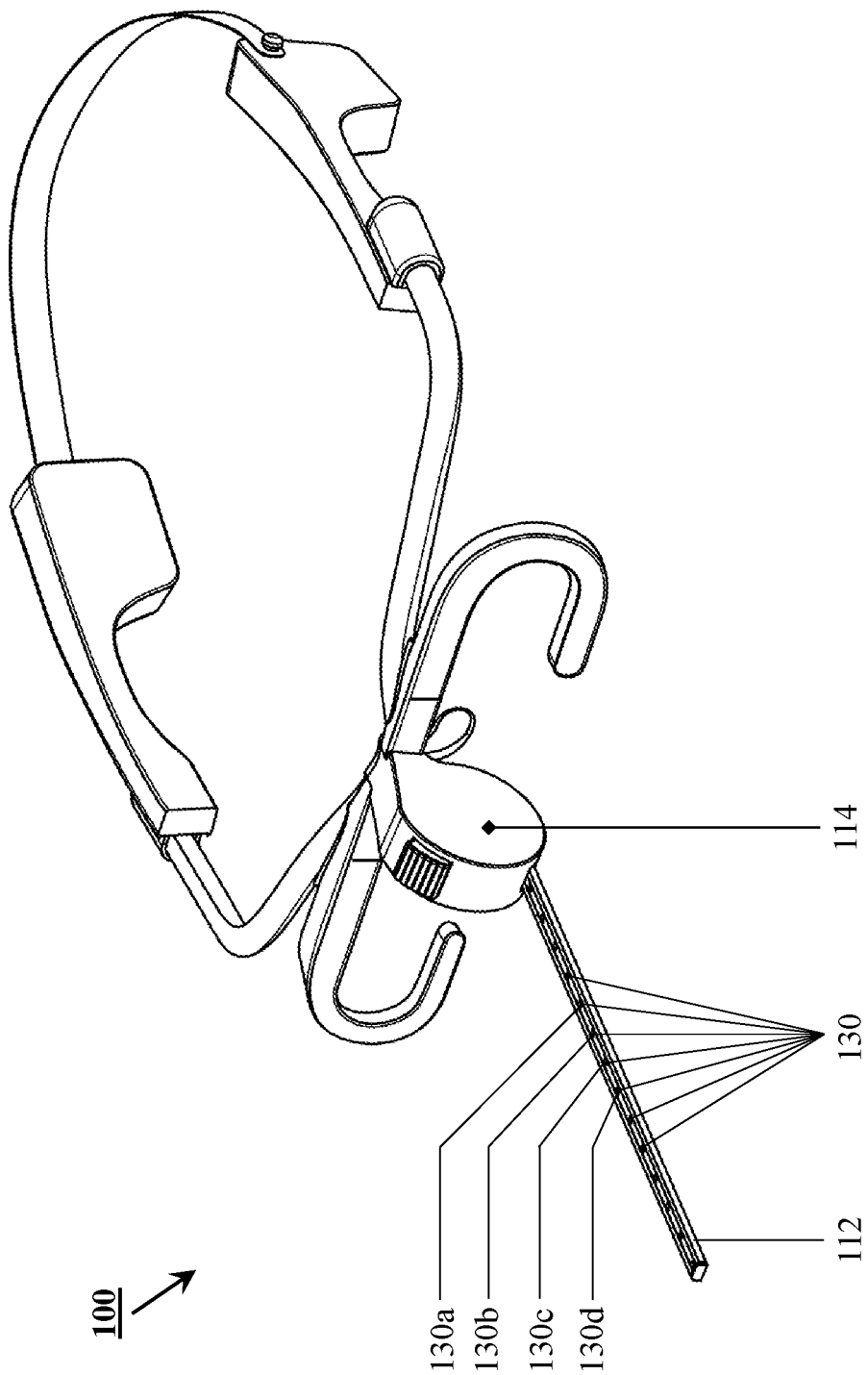
FIG. 1B illustrates a front perspective view of the wearable device of FIG. 1A.

FIG. 1B illustrates a front perspective view of the wearable device 100 of FIG. 1A. As illustrated in FIG. 1B, the longitudinal member 112, which is extending from the housing 114, includes a plurality of colored light sources 130 arranged to be viewable by both eyes of the user. The plurality of colored light sources 130 is configured to emit electromagnetic radiation in the visible light band (380-700 nm) of the electromagnetic spectrum. In several embodiments, the plurality of colored light sources 130 is configured to emit electromagnetic radiation with wavelengths ranging between 630 nm-680 nm. In several embodiments of the present invention, the plurality of colored light sources 130 are separated from each other by a distance varying between 2 inches and 5 inches, along with the longitudinal member 112.

Further, in accordance with another embodiment of the present invention and taking the reference from the "Brock String", the longitudinal member 112 includes a plurality of colored light sources 130, connected by a white stripe. Because the phenomenon of physiological diplopia causes objects outside the point of fixation to be seen as double, the user 510 can see specifically where their eyes and mind are aiming, and whether their eyes are working together efficiently as a team. The Brock string is commonly employed during the treatment of convergence insufficiency and other anomalies of binocular vision. It is used to develop skills of convergence as well as to disrupt suppression of one of the eyes.

The controller 116 is envisaged to be connected with the plurality of colored light sources 130 and the plurality of therapeutic light sources 110. Also, the controller 116 is configured to sequentially control the display of each of the plurality of colored light sources 130, arranged in a linear arrangement, to both eyes of the user.

The eye adjusts its focusing power in response to both changes in color and distance. The location of the displayed light source in a horizontal plane relative to the observer is also changing, exercising the ability of the eyes of the user to move freely and accurately in the horizontal plane as the eyes track the movement of the displayed light source. The horizontal plane here refers to the plane of the top surface of the longitudinal member 112 which extends parallel to the ground. Moreover, providing light therapy during vision training can maximize the benefits of vision training, causing the overall effect to be more than the sum of its parts. In that regard, in several embodiments, the plurality of therapeutic light sources 110 is configured to emit electromagnetic radiation with wavelengths in the range of 630 nm to 880 nm. As a result, when the user would look through the left 104 and the right 106 rims, they will see a red-colored circle surrounding their view. Even though each eye would only see a part of the circle, the brain of the user would fuse those two images to generate the one complete circle, in predominantly red color, surrounding everything they are looking at. The therapeutic value of the circle is that it would create a virtual sight in space that would immediately improve the ability of the user to aim their eyes, significantly improving their attention and performance. This effect would be akin to the effect created by iron and telescopic sights when used in the context of rifles and other firearms when intended to improve the accuracy of hitting an intended target. As an advantage, the user can train their eyes to aim at a high level, and have that skill transfer to their everyday activities.

Figure 1C:
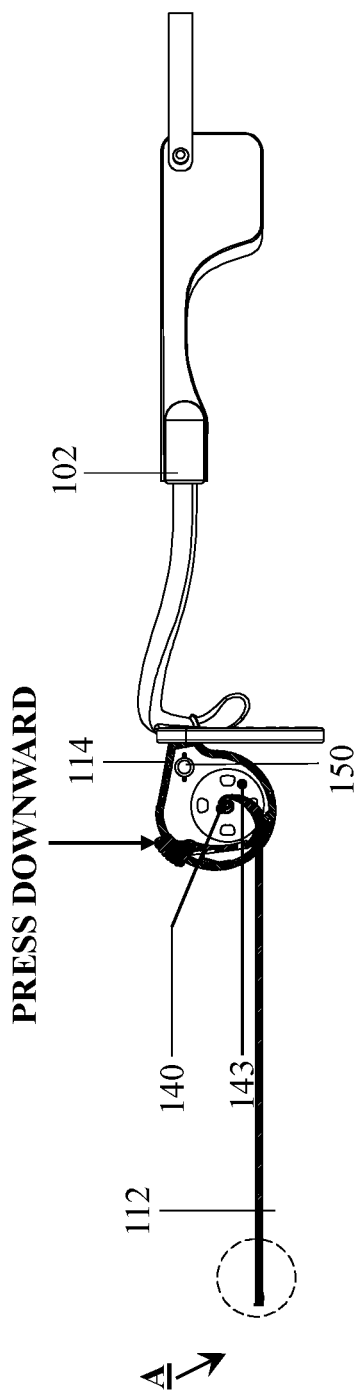
FIG. 1C illustrates a central sectional view of the wearable device of FIG. 1A.

FIG. 1C illustrates a central sectional view of the wearable device 100 of FIG. 1A. As illustrated in FIG. 1C, the longitudinal member 112 is extendible through an extension mechanism 140 attached with the spectacle frame 102. The longitudinal member 112 and the extension mechanism 140 have been provided within the housing 114 of the wearable device 100. The longitudinal member 112 is envisaged to be flexible and capable of being rolled onto a coil spring 143 without developing creases or kinks in the material of the longitudinal member 112. Therefore, by making the housing 114 adapted to be detachably attached with the spectacle frame 102, the longitudinal member 112 and the extension mechanism 140 can also be made to be detachably attached with the spectacle frame 102. This would make the overall wearable device 100 multi-purpose and modular (through the attachment of several different kinds of training modules housed in different housings 114), and also easy to transport and store. The detachment of the housing 114 would also allow the wearable device 100 to be used as a standalone eye therapy device, thereby increasing the utility of the wearable device 100. The attachment and detachment of the housing 114 can be achieved through snap-fit arrangements, loop, and hook fasteners based arrangements, spring-loaded clips based arrangements, and magnetic coupling based arrangements, etc.

Furthermore, there is shown a sound transducer 150 illustrated in FIG. 1C, provided within the housing 114 of the wearable device 100. At the beginning of each vision training and therapy session, the sound transducer 150 will emit a short 'beep' sound three times with an interval of one second. The initial three beeps of the sound transducer 150 allow the user 510 to position the wearable device 100 and get ready to start the session. These short 'beep' sounds will be followed by a long "beep" sound, which in turn initiates the illumination of the therapeutic light sources 110 and colored light sources 130 of the wearable device 100. The colored light sources 130 will illuminate one by one beginning from the one end which may be the nearest end or the farthest end of the longitudinal member 112 depends upon the illumination sequence determined by the user 510. Each time the colored light source 130 is turned on, the sound transducer emits a short 'beep' sound.

The sound transducer 150 is further envisaged to be controlled by the controller 116, where a program or a software creates the different frequencies by turning it on and off at the frequency of desired pitch. In an exemplary embodiment, the sound preceding each session may have an audio pulse of 250 milliseconds at 250 hertz and the sound before and after each session may have an audio pulse of 750 milliseconds at 250 hertz. Employing the sound transducer 150 as an auditory stimulus in the wearable device 100 will empower or reinforces the visual experience of the user 510.

Figure 1D:
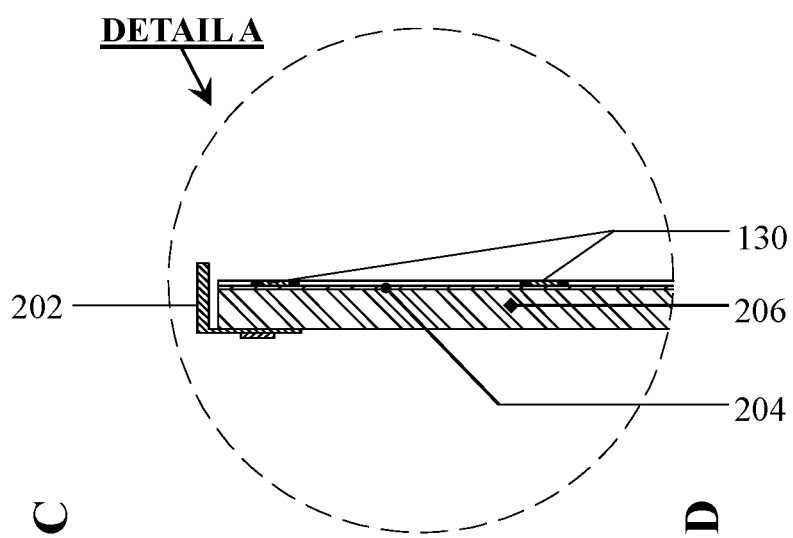
FIG. 1D illustrates a detailed view of a portion of the wearable device of FIG. 1C.

FIG. 1D illustrates a detailed view of a portion 'A' of the wearable device 100 of FIG. 1C. FIG. 1D illustrates the plurality of colored light source 130 in form of LEDs provided on a flexible Printed Circuit Board (PCB) 204. The flexible PCB 204 has been provided onto a flexible substrate layer 206. The flexible substrate layer 206 may be made up of silicones such as Poly Di-Methyl-Siloxane (PDMS). A hook 202 has been provided at a distal end of the longitudinal member 112 that prevents wear of the distal end of the longitudinal member 112 and acts as a handle while extending the longitudinal member 112.

Figure 2:
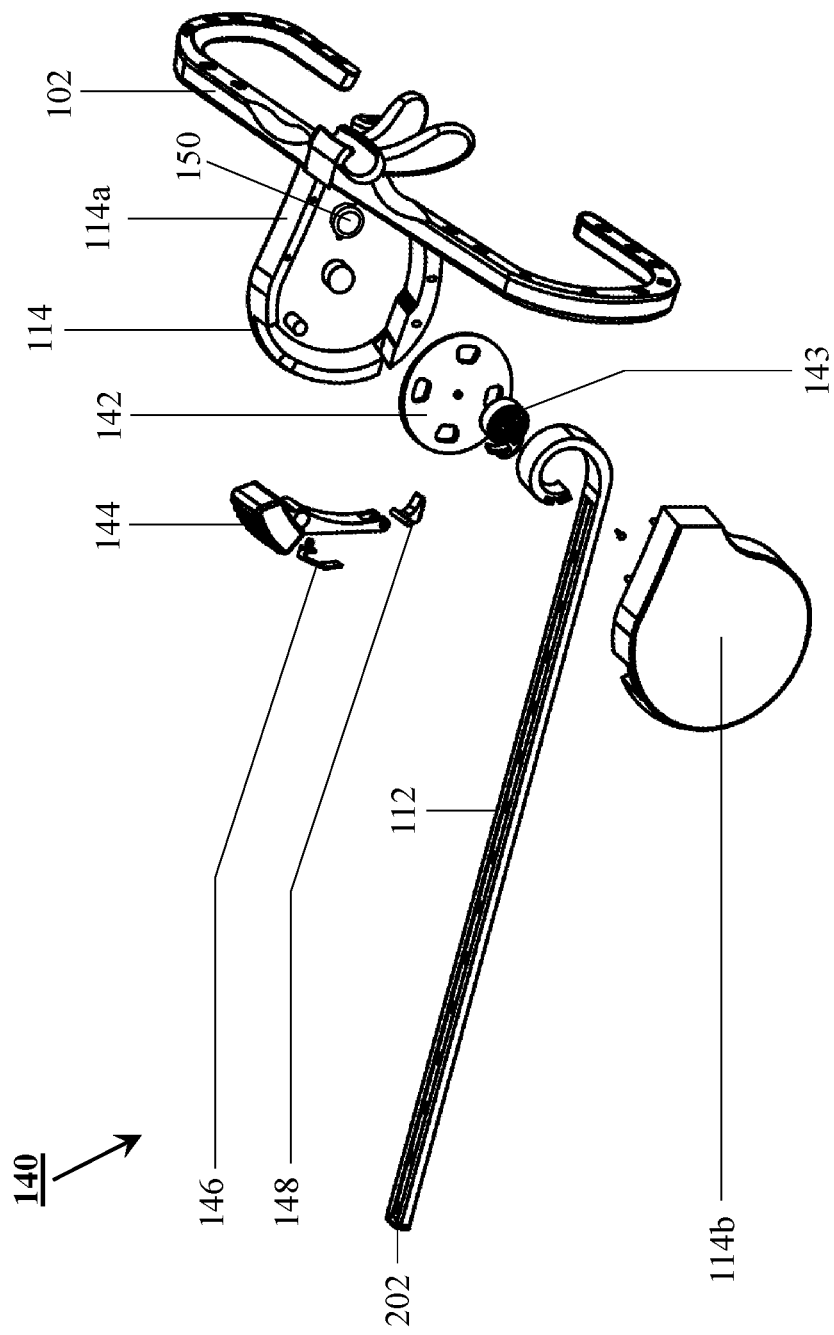
FIG. 2 illustrates an exploded view of an extension mechanism of the wearable device of FIG. 1A.

FIG. 2 illustrates an exploded view of the extension mechanism 140 of the wearable device 100 of FIG. 1A. The extension mechanism 140 has been primarily housed in the housing 114 which has two split halves 114a and 114b. The extension mechanism 140 includes a spool 142 that is adapted to roll in and roll out the longitudinal member 112 onto the coil spring 143. A locking button 144 is connected to a locking arrester 148 via a flexible member 146 that acts as a spring. The flexible member 146 is adapted to keep the locking arrester 148 biased against the longitudinal member 112, preventing any change in length of the longitudinal member 112 and also preventing the coil spring 143 from rolling back the longitudinal member 112 when the wearable device 100 is being used. However, when the locking button 144 is pressed downward, a convex shape of the flexible member 146 causes the locking arrester 148 to move upwards and release the longitudinal member 112. This allows the longitudinal member 112 to be extended, manually or through an actuator mechanism, against the pulling force exerted by the coil spring 143, or contracted automatically because of the pulling force exerted by the coil spring 143. The hook 202 prevents the longitudinal member 112 from getting completely rolled in the spool 142, and onto the coil spring 143, thus ensuring permanent access to the longitudinal member 112.

The extension mechanism 140 may also be operated through pneumatic means, allowing electronic control of the extension mechanism 140. The electronic control of the extension mechanism 140 not only reduces the manual effort required in the operation of the extension mechanism 140 but also allows the extension mechanism 140 to be controlled remotely via a communication network, that may be wired or wireless. In several alternate embodiments, the extension mechanism 140 may also include electrical motors or rotary or linear kinds, without departing from the scope of the invention.

Figure 3A:
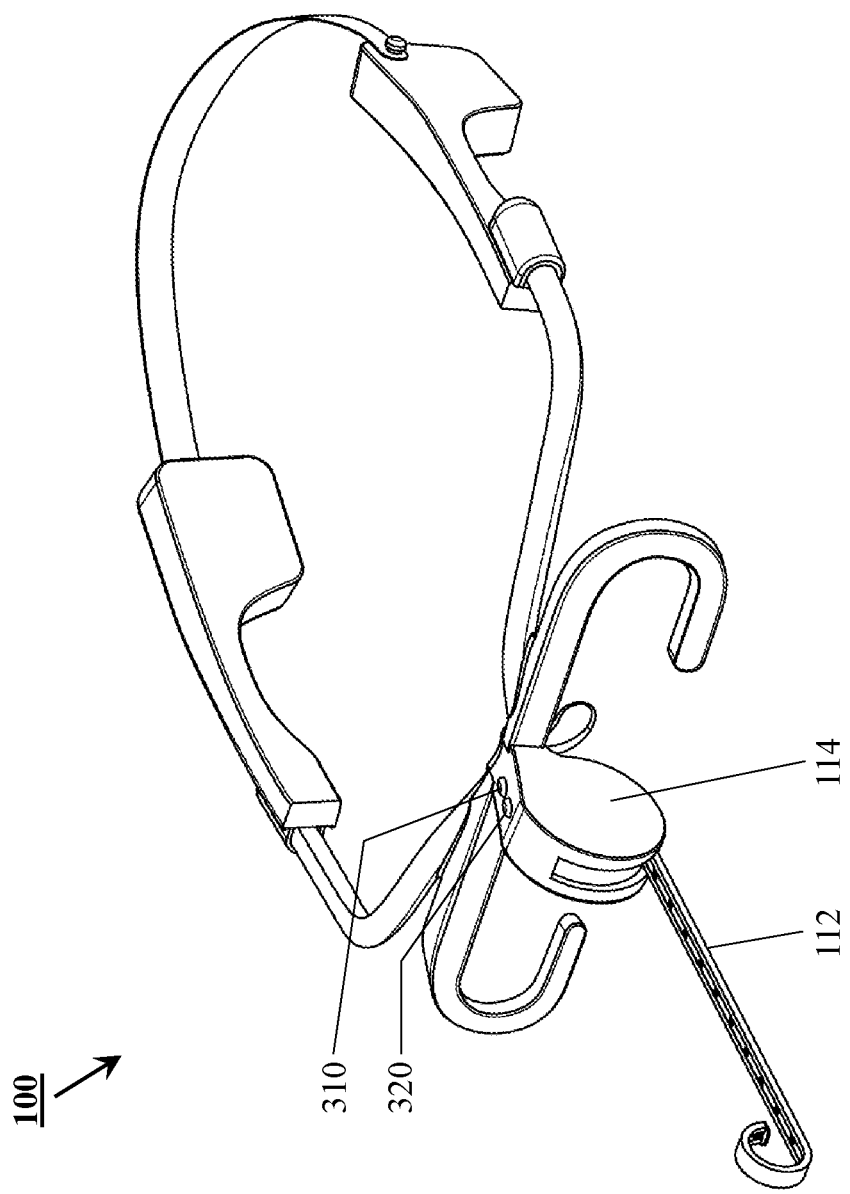
FIG. 3A illustrates a front perspective view of a wearable device for vision training and therapy, in accordance with another embodiment of the present invention.

FIG. 3A illustrates a front perspective view of a wearable device 100 for vision training and therapy, in accordance with another embodiment of the present invention. The extension mechanism 140 encased in the housing 114 of the wearable device 100 of FIG. 3A is adapted to be operated pneumatically. Therefore, an outer surface of the housing 114 has been provided with a pressure create switch 310 and a pressure release switch 320. FIG. 3B illustrates a central sectional view of the wearable device 100 of FIG. 3A, depicting the pneumatic components of the extension mechanism 140. FIG. 3C illustrates a detailed view of a portion 'B' of the wearable device 100 of FIG. 3B. As depicted in FIG. 3C, the flexible substrate layer 206 further includes an air cavity 332 for receiving compressed air for extension of the longitudinal member 112.

Figure 4:
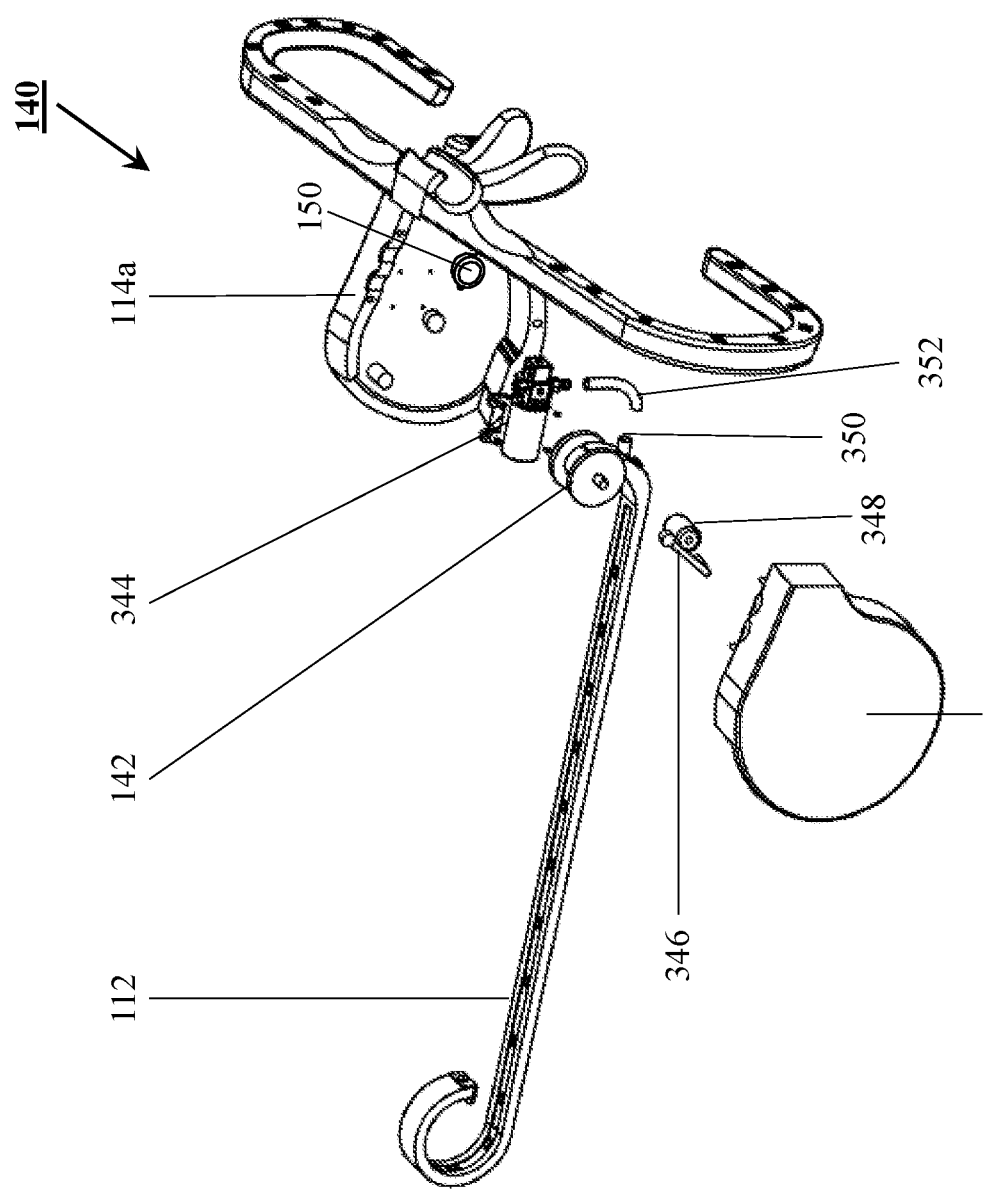
FIG. 4 illustrates an exploded view of an extension mechanism of the wearable device of FIG. 3A.

FIG. 4 illustrates an exploded view of the extension mechanism 140 of the wearable device 100 of FIG. 3A. In addition to the spool 142 and the two halves 114*a* and 114*b*, the extension mechanism 140 also include a pneumatic pump 344 configured to generate pressurized air, an air inlet pipe 352 connecting the pneumatic pump 344 with an inlet nozzle 350 provided at an inlet to the air cavity 332 of the longitudinal member 112. The pneumatic pump 344 is envisaged to be a micro-pneumatic pump of mechanical or non-mechanical construction, depending upon the application of the wearable device 100. The supply of pressurized air from the pneumatic pump 344 into the air cavity 332 causes the longitudinal member 112 to extend. While, the release of the air pressure from the pneumatic pump 344 causes the air to escape from the air cavity 332, causing the longitudinal member 112 to contract and roll in onto the spool 142. A guiding pulley 348 provided below the longitudinal member 112 is adapted to guide the extension and contraction of the longitudinal member 112. Also, a lever 346 is adapted to lock the longitudinal member 112 once the longitudinal member 112 has been extended to a predetermined length.

Figure 5:
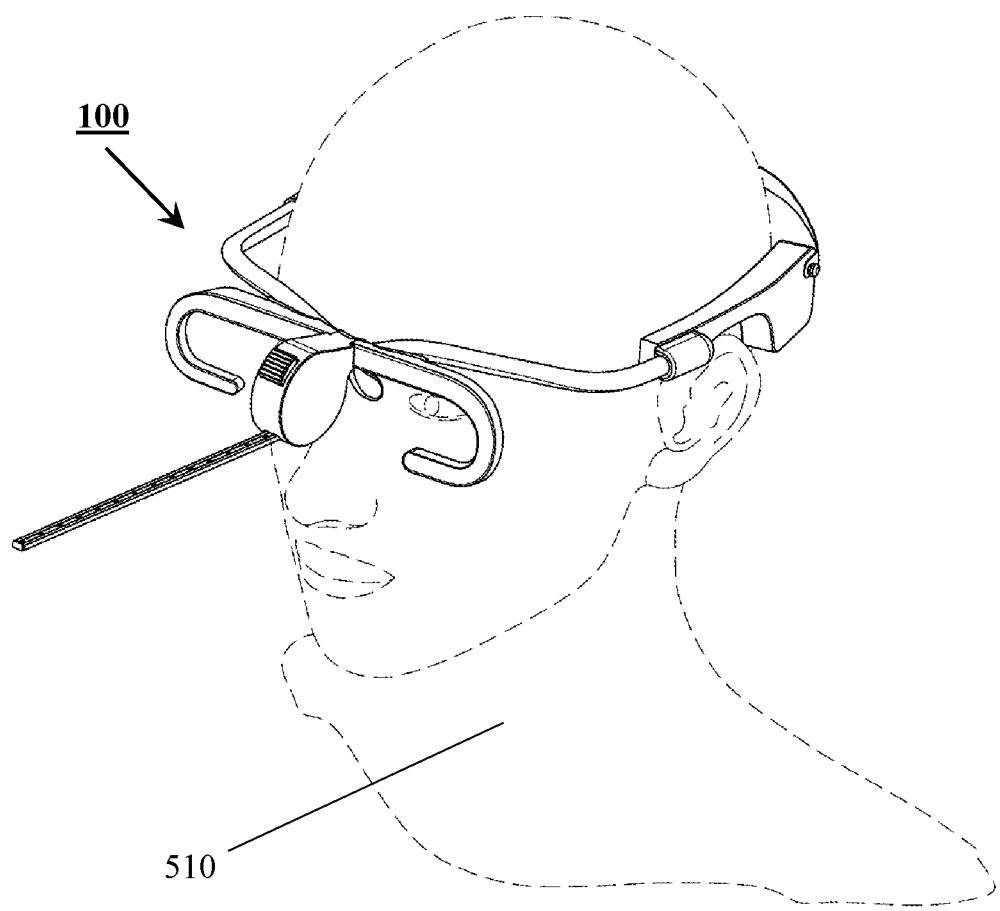
FIG. 5 illustrates a user wearing a wearable device for vision training and therapy, in accordance with an embodiment of the present invention.

FIG. 5 illustrates a user 510 wearing the wearable device 100 for vision training and therapy, in accordance with an embodiment of the present invention. In several embodiments, the controller 116 is further configured to control the emission characteristics, such as intensity, frequency, mode of operation, and scheduling, of the plurality of therapeutic light sources 110 and the plurality of colored light sources 130 in response to user input. In that regard, the user input is received through the control interface 118 provided with the wearable device 100.

Figure 6A:
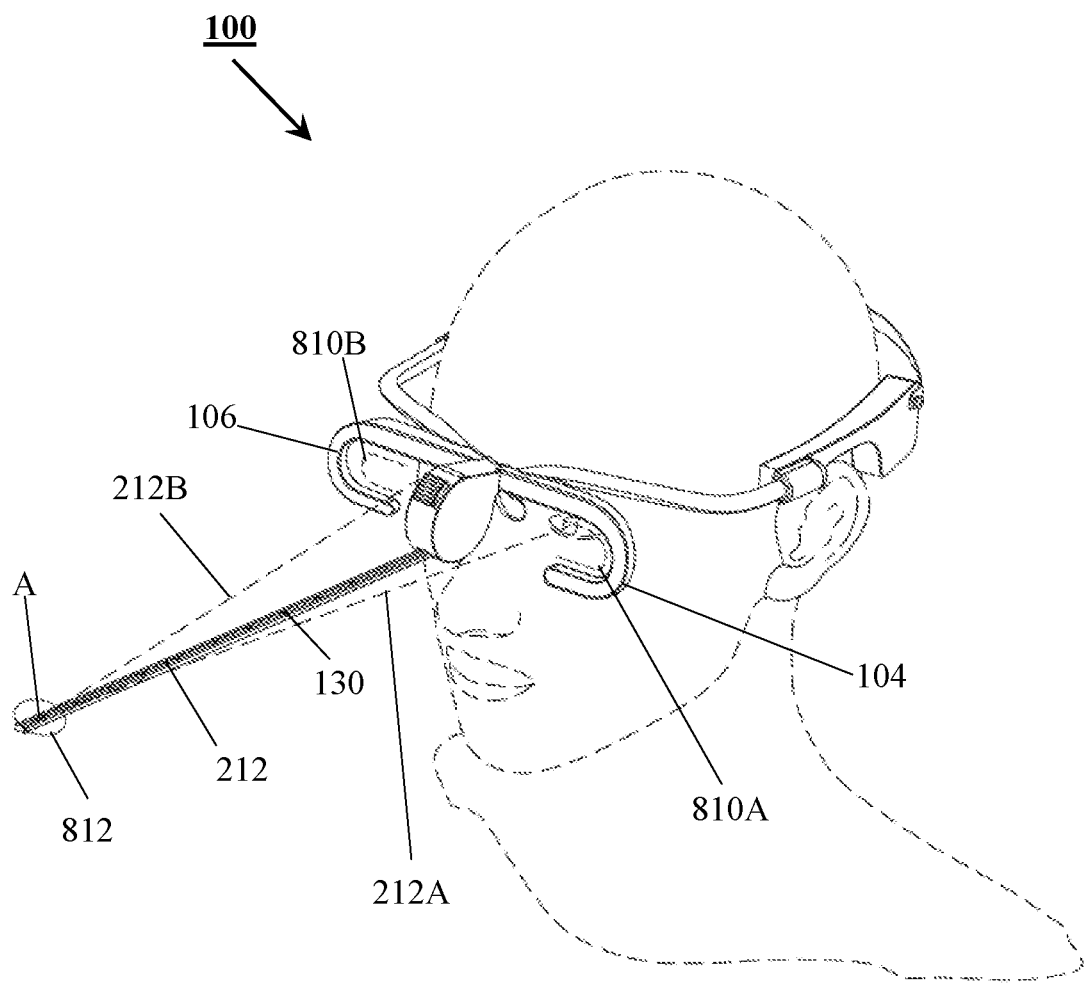
FIG. 6A illustrates the positioning of the eyes, when the user fixates the distant light sources, in accordance with another embodiment of the present invention.
Figure 6B:
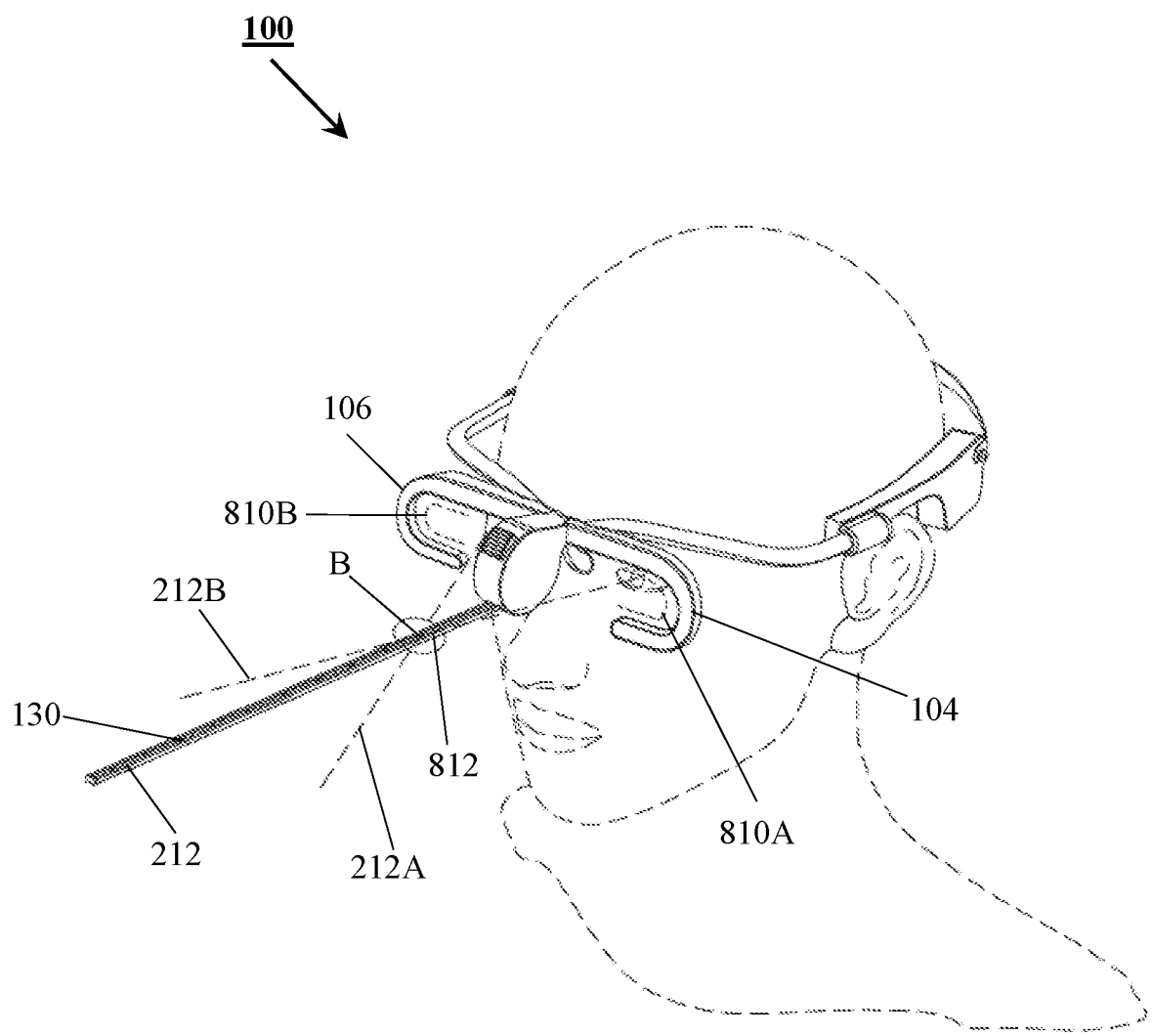
FIG. 6B illustrates the positioning of the eyes, when the user fixates the near light sources, in accordance with another embodiment of the present invention.

FIG. 6A and FIG. 6B illustrate the visual alignment of the eyes when combined with "Brock string", in accordance with another embodiment of the present invention. According to this embodiment, the longitudinal member 112 includes a plurality of colored light sources 130, connected by a white stripe 212. The white strip 212 is mounted on the upper surface of the longitudinal member 112. When the wearable device 100 is activated and worn by the user 510 on their head, a pair of virtual half circles (810A, 810B) are formed by the rims 104 and 106, and thereby creating the appearance of a virtual circle 812 in space surrounding the light source being viewed, that is parallel to the rims of the spectacle frame 102. The left half circle 810A and right half circle 810B are created by the therapeutic light sources 110 positioned on the left rim 104 and right rim 106 of the spectacle frame 102, emitting radiation preferably in the visible range. When user 510 sees the colored light source 130 provided on the longitudinal member 112, a virtual circle 812 will appear surrounding the colored light source 130, immediately improving the ability of the user's eyes and mind to accurately aim and attend to whatever they are looking at.

When the user 510 sees at the distant light source 'A' through the virtual half circles (810A, 810B) created by the left rim 104 and right rim 106 respectively, the user 510 will see two virtual white stripes (212A and 212B) wherein each of which appears to be a frontal projection coming from the user's eyes and intersecting at a fixation point (at 'A') forming a 'V' shaped illusion (illustrated in FIG. 6A). Also, when the user 510 sees at the near light source 'B', the user 510 will see two virtual white stripes (212A and 212B) which are intersecting at a fixation point (at 'B') forming an 'X' shaped illusion (illustrated in FIG. 6B). The two virtual white stripes (212A and 212B) depicting the user's line of sight are created by the actual white stripe 212 connecting the plurality of colored light sources 130. Further, the 'V' and 'X' illusions are created by the two virtual white stripes (212A and 212B) projecting out of the user's 510 eyes, allowing the user 510 to see exactly where each eye is looking at, and whether his eyes are working together efficiently as a team. Also, allowing the user to determine whether his mind and eyes are focusing at the same place at the same time.

The colored light source 130 being viewed is where the mind is focused and the point where both virtual white stripes (212A and 212B) converge is where the eyes are aiming. If the colored light source 130 being viewed appears doubled, or if at times one of the virtual white stripes (212A and 212B) disappears, it indicates the two eyes are having difficulty working together or that one of the eyes stopped working at times. The combinational effect which is achieved by the virtual circle 812 in space and the 'V, X' shaped illusions, improves the ability of the user's eyes and mind to accurately aim and attend to whatever he/she is looking at.

Figure 7:
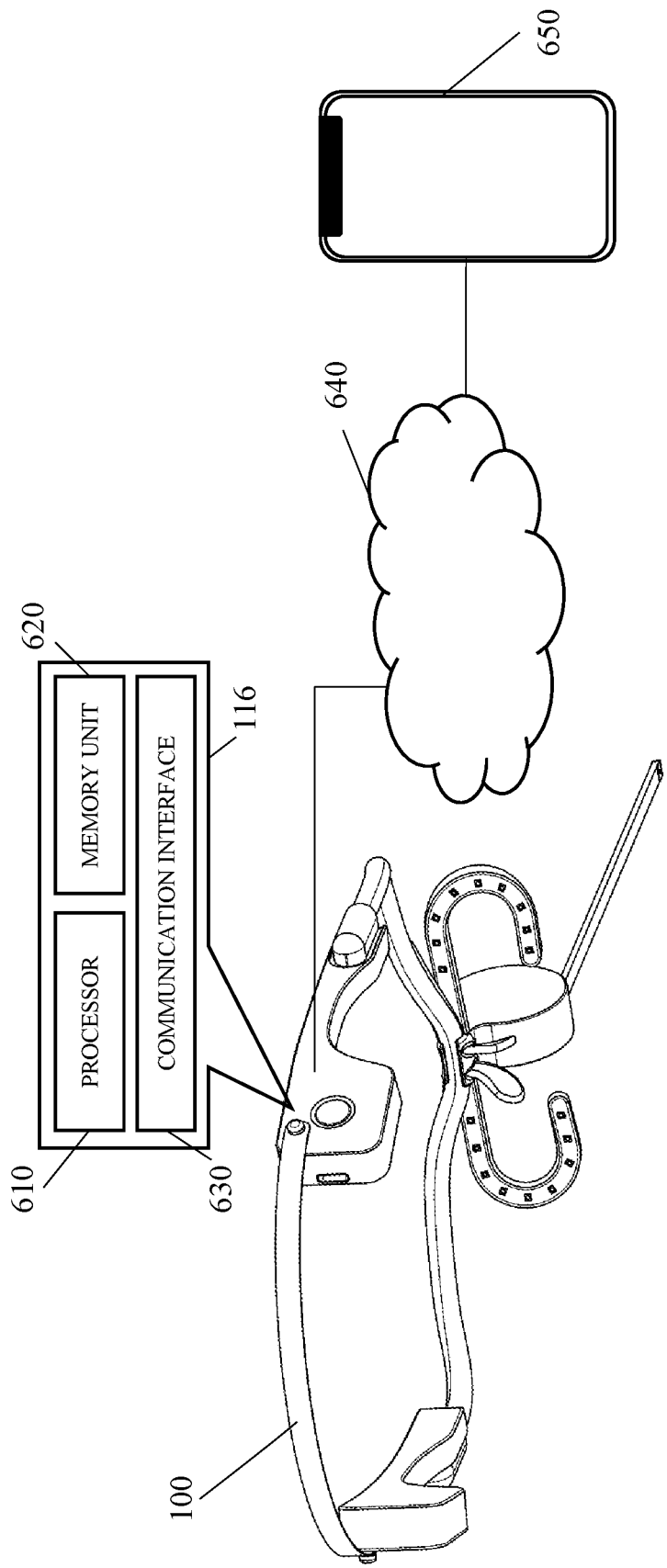
FIG. 7 illustrates a wearable device for vision training connected with a remote communication device, in accordance with an embodiment of the present invention.

FIG. 7 illustrates the wearable device 100 for vision training connected with a remote communication device 650, in accordance with an embodiment of the present invention. The remote communication device 650 may be a smartphone, a desktop computer, a tablet, a Personal Digital Assistant (PDA), a smartwatch, or the like. Further, the remote communication device 650 is connected with the wearable device 100 through a communication network 640. The controller 116 is envisaged to include a processor 610, a memory unit 620, and a communication interface 630 that allows the controller 116 to communicate with the remote communication device 650, via the communication network 640. In that regard, the user input, for the control of the emission characteristics, may also be received from the remote communication device 650.

Figure 8:
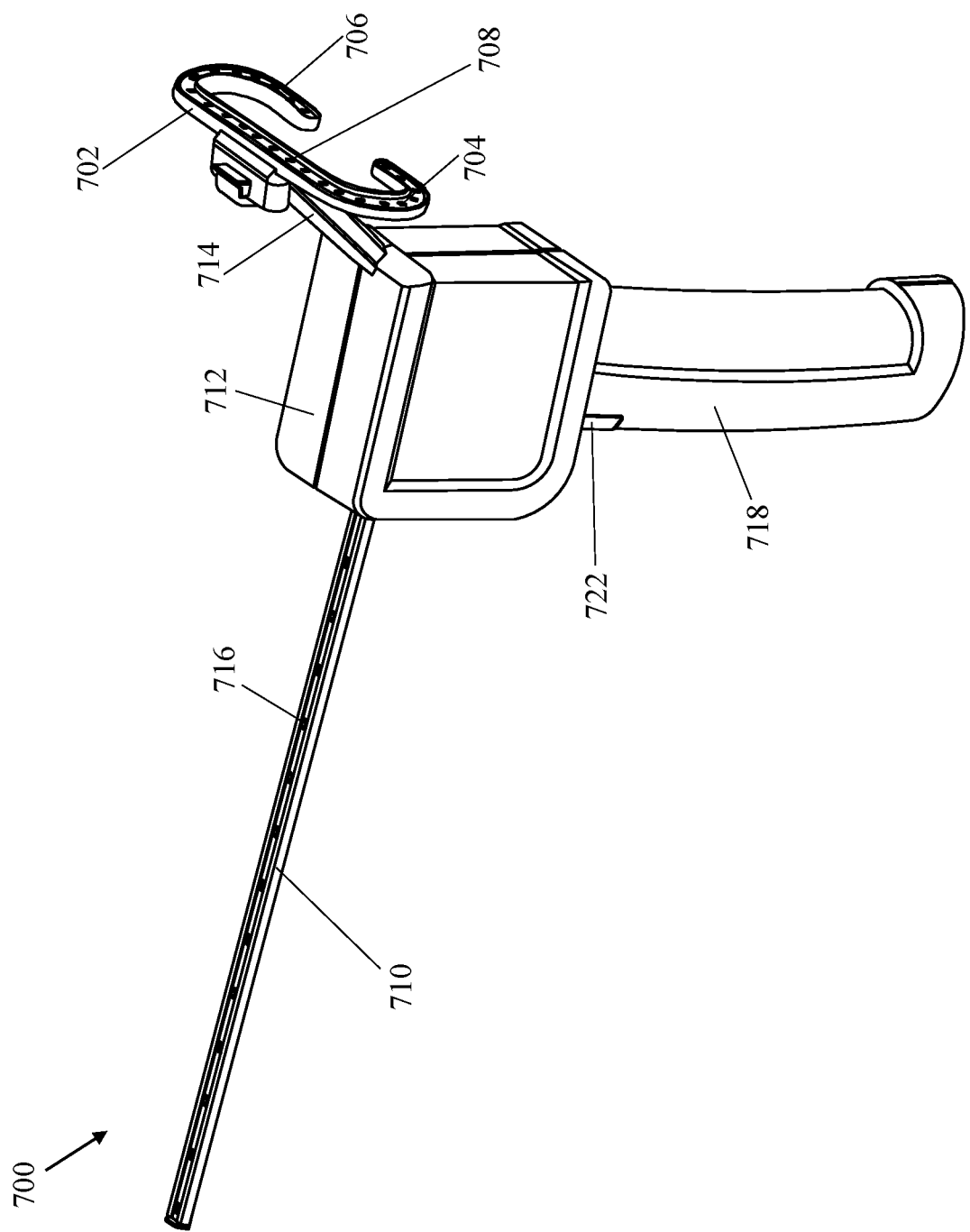
FIG. 8 illustrates a handheld device for vision training and therapy, in accordance with an alternate embodiment of the present invention.

FIG. 8 illustrates a perspective view of a handheld device 700 for vision training and therapy, in accordance with an alternate embodiment of the present invention. As illustrated in FIG. 7, the handheld device 700 includes a spectacle frame 702 with a left rim 704 and a right rim 706. The left rim 704 and the right rim 706 include a plurality of therapeutic light sources 708 positioned at the periphery of both rims and emits therapeutic radiation towards the surrounding area of the user's eye. The therapeutic light sources 708 are positioned at equidistance to each other. The handheld device 700 further includes a longitudinal member 710 extending from a housing 712 that is connected with the spectacle frame 702 through a connecting member 714.

The longitudinal member 710 is located below the spectacle frame 702, and extends away from the housing 712, along the line of sight of the user. The longitudinal member 710 is extendible from the housing 712 through the extension mechanism as described in the preferred embodiment of the present invention. The longitudinal member 710 includes a plurality of colored light sources 716 that emits radiation in the visible range of the electromagnetic spectrum and is arranged to be viewable by both eyes of the user through left rim 704 and right rim 706 respectively. The colored light sources 716 are sequentially emitting radiation to provide a plurality of vision training exercises which helps in the optimization of visual skills.

Figure 9:
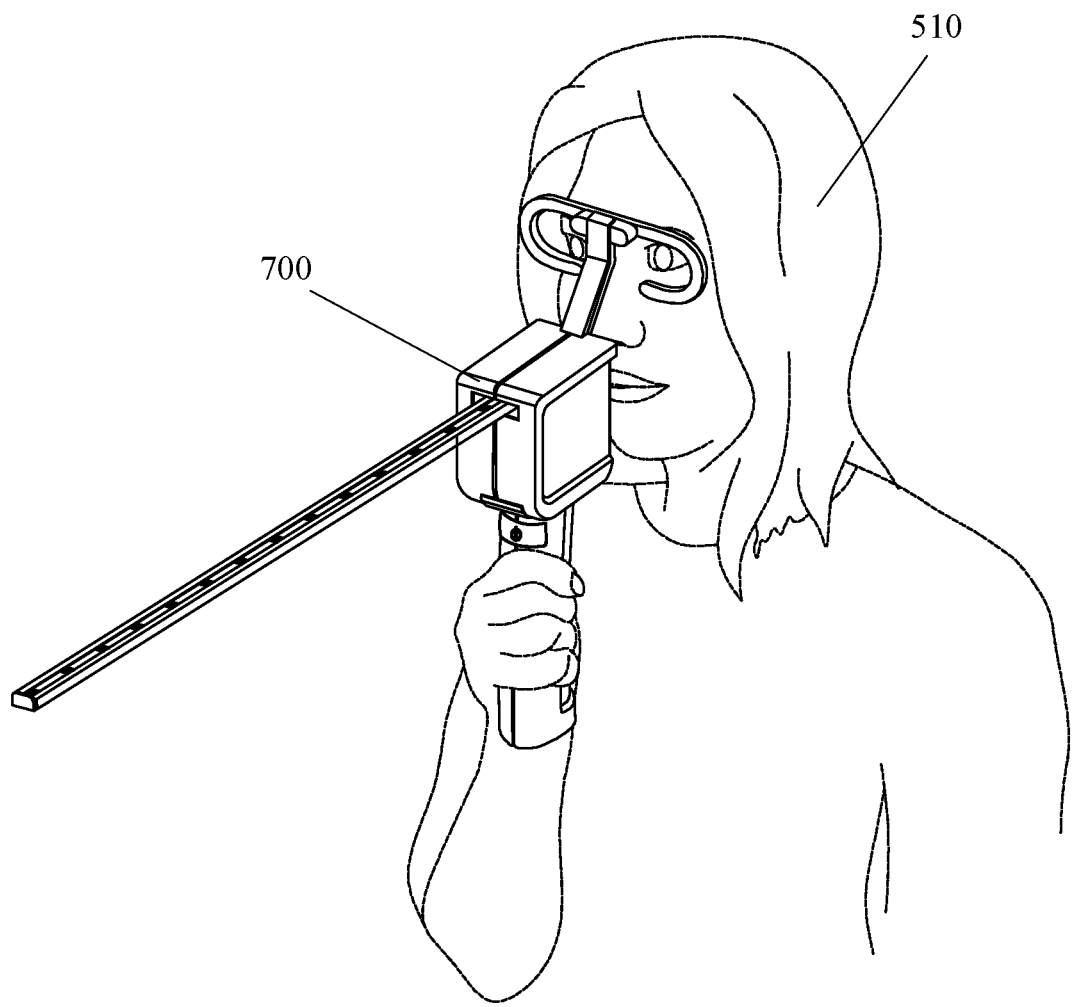
FIG. 9 illustrates a user using the handheld device which is illustrated in FIG. 7 of the present invention.
Figure 10:
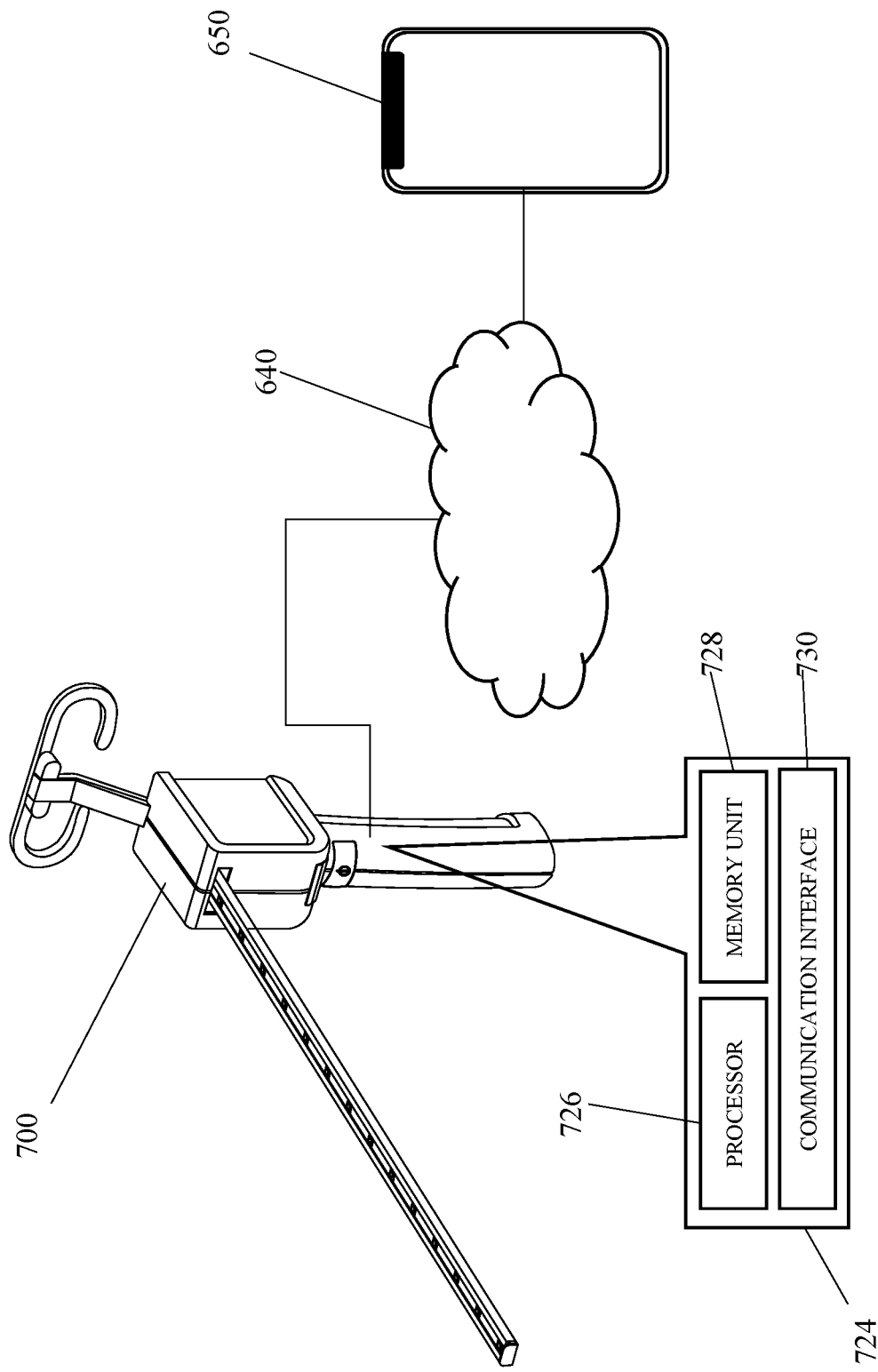
FIG. 10 illustrates a remote communication device connected with the handheld device disclosed in FIG. 7 of the present invention, through a communication network.

The handheld device 700 further includes a handle 718 which is gripped by a user 510 (shown in FIG. 9), connected to the housing 712 of the handheld device 700. The handle 718 allows the user 510 to use the handheld device 700 at more ease and comfort. In this embodiment, the user 510 doesn't need to wear the handheld device 700 during vision training and therapy session. The handle 718 comprises a main switch 722 to turn on/off the handheld device 700 provided at the outer surface of handle 718, and a controller 724 for controlling the overall functioning of the handheld device 700. The controller 724 is configured to control the emission characteristics of the plurality of therapeutic light sources 708 and also sequentially control the display of each of the plurality of colored light sources 716. The controller 724 includes a processor 726, a memory unit 728, and a communication interface 730 that allows the controller 724 to communicate with the remote communication device 650, via the communication network 640 (shown in FIG. 10). FIG. 10 illustrates the handheld device 700 for vision training connected with the remote communication device 650. The remote communication device 650 may be a smartphone, a desktop computer, a tablet, a Personal Digital Assistant (PDA), or the like.

The embodiments of the invention as described above offer several advantages including simplicity in design and construction, novel and inventive use of readily available materials and equipment. Further, the incorporation of LEDs as the radiation source provides significant power economies. The same construction of the wearable device and handheld device can be used for multiple applications, such as therapeutic or professional sports training, with minor programming modifications. Moreover, the operation of the device does not demand special skills on the part of the user or the operator and is therefore suited for both domestic applications (where convenience is the key) and commercial applications (where the economy is the key).

The invention claimed is:

1. A wearable device for vision training and therapy, the device comprising:
   a spectacle frame including a left rim, a right rim, and a bridge connecting the left rim and the right rim, wherein the left rim and the right rim include a plurality of therapeutic light sources located along the left rim and the right rim, for providing light therapy to both eyes of a user;
   a longitudinal member connected with the spectacle frame, located below the bridge of the spectacle frame, and extending away from the spectacle frame, along a line of sight of the user, wherein the longitudinal member includes a plurality of colored light sources connected by a white stripe arranged to be viewable by both of the eyes of the user; and
   a controller connected with the plurality of therapeutic light sources and the plurality of colored light sources;
   wherein the controller is configured to sequentially control a display of each of the plurality of colored light sources, arranged in a linear arrangement, to both eyes of the user; and
   wherein the longitudinal member is extendible through an extension mechanism attached with the spectacle frame.

2. The device as claimed in claim 1, wherein the plurality of therapeutic light sources is configured to emit electromagnetic radiation with wavelengths in a range of 630 nm to 880 nm.

3. The device as claimed in claim 1, wherein the longitudinal member and the extension mechanism are included in a housing detachably attached with the spectacle frame.

4. The device as claimed in claim 3, wherein an attachment and a detachment of the housing are adapted to be achieved through one or more of a snap-fit arrangement, loop and hook fasteners based arrangement, spring loaded clips based arrangement, and magnetic coupling based arrangements.

5. The device as claimed in claim 1, wherein the extension mechanism further includes:
   a spool including a coil spring adapted to roll out and roll in the longitudinal member;
   a locking button connected with a locking arrester via a flexible member;
   wherein the flexible member is adapted to keep the locking arrester biased against the longitudinal member; and
   wherein, in use, when the locking button is pressed downward, a convex shape of the flexible member is adapted to cause the locking arrester to move upwards and release the longitudinal member.

6. The device as claimed in claim 1, wherein the extension mechanism further includes:
   a spool adapted to roll out and roll in the longitudinal member;
   a pneumatic pump configured to generate pressurized air; and
   an air inlet pipe connecting the pneumatic pump with an inlet nozzle provided at an inlet to an air cavity of the longitudinal member; and
   a lever is adapted to lock the longitudinal member once the longitudinal member has been extended to a predetermined length;
   wherein, in use, a supply of pressurized air from the pneumatic pump into the air cavity is adapted to cause an extension of the longitudinal member.

7. The device as claimed in claim 1, wherein the plurality of therapeutic light sources are configured to emit electromagnetic radiation in an infrared range of wavelengths of the electromagnetic spectrum.

8. The device as claimed in claim 1, wherein the plurality of therapeutic light sources are separated from each other by a distance varying between 0.002 inches and 0.08 inches, along the left rim and the right rim.

9. The device as claimed in claim 1, wherein the plurality of colored light sources are separated from each other by a distance varying between 2 inches and 5 inches, along with the longitudinal member.

10. The device as claimed in claim 1, wherein the plurality of therapeutic light sources and the plurality of colored light sources include a plurality of Light Emitting Diodes (LEDs).

11. The device as claimed in claim 1, wherein the controller is further configured to control emission characteristics of the plurality of therapeutic light sources and the plurality of colored light sources in response to user input.

12. The device as claimed in claim 11, wherein the user input is received through a control interface provided with the device.

13. The device as claimed in claim 11, wherein the user input is received from a remote communication device connected with the device through a communication network.

14. A handheld device for vision training and therapy, the device comprising:
   a spectacle frame including a left rim, a right rim, and a bridge connecting the left rim and the right rim, wherein the left rim and the right rim include a plurality of therapeutic light sources located along the left rim and the right rim, for providing light therapy to both eyes of a user;
   a longitudinal member connected with the spectacle frame, located below the bridge of the spectacle frame, and extending away from the spectacle frame, along a line of sight of the user, wherein the longitudinal member includes a plurality of colored light sources connected by a white stripe arranged to be viewable by both of the eyes of the user; and a controller connected with the plurality of therapeutic light sources and the plurality of colored light sources;

wherein the controller is configured to sequentially control a display of each of the plurality of colored light sources, arranged in a linear arrangement, to both eyes of the user; and wherein the longitudinal member is extendible through an extension mechanism attached with the spectacle frame.

\* \* \* \* \*